United States Patent
Rueter

(10) Patent No.: US 7,783,355 B2
(45) Date of Patent: Aug. 24, 2010

(54) DYNAMIC ADJUSTMENT OF CAPTURE MANAGEMENT "SAFETY MARGIN"

(75) Inventor: John C. Rueter, Woodbury, MN (US)

(73) Assignee: Medtronic, Inc., Minneapolis, MN (US)

( * ) Notice: Subject to any disclaimer, the term of this patent is extended or adjusted under 35 U.S.C. 154(b) by 1115 days.

(21) Appl. No.: 10/761,473

(22) Filed: Jan. 21, 2004

(65) Prior Publication Data

US 2005/0159785 A1    Jul. 21, 2005

(51) Int. Cl.
*A61N 1/37* (2006.01)
(52) U.S. Cl. ............................................. 607/28; 607/9
(58) Field of Classification Search ............... 607/9, 607/11, 27, 28, 29
See application file for complete search history.

(56) References Cited

U.S. PATENT DOCUMENTS

| | | | |
|---|---|---|---|
| 4,726,380 A | 2/1988 | Vollmann et al. | 128/419 PG |
| 4,830,006 A | 5/1989 | Haluska et al. | 128/419 PG |
| 4,880,005 A | 11/1989 | Pless et al. | 128/419 PG |
| 4,932,406 A | 6/1990 | Berkovits | 128/419 PG |
| 4,944,298 A | 7/1990 | Sholder | 128/419 PG |
| 5,144,949 A | 9/1992 | Olson | 128/419 PG |
| 5,201,865 A | 4/1993 | Kuehn | 128/419 PT |
| 5,318,594 A | 6/1994 | Limousin et al. | 607/9 |
| 5,507,782 A | 4/1996 | Kieval et al. | 607/9 |
| 5,545,186 A | 8/1996 | Olson et al. | 607/14 |
| 5,601,615 A | 2/1997 | Markowitz et al. | 607/28 |
| 5,713,933 A | 2/1998 | Condie et al. | 607/28 |
| 5,741,311 A | 4/1998 | McVenes et al. | 607/28 |
| 5,755,736 A | 5/1998 | Gillberg et al. | 607/4 |
| 5,861,012 A * | 1/1999 | Stroebel | 607/28 |
| 5,991,656 A | 11/1999 | Olson et al. | 607/4 |
| 6,061,594 A | 5/2000 | Zhu et al. | 607/28 |
| 6,067,472 A | 5/2000 | Vonk et al. | 607/28 |
| 6,317,633 B1 * | 11/2001 | Jorgenson et al. | 607/28 |
| 6,430,441 B1 | 8/2002 | Levine | 607/28 |
| 6,456,879 B1 | 9/2002 | Weinberg | 607/11 |
| 6,456,882 B1 * | 9/2002 | Schloss | 607/28 |
| 6,549,806 B1 * | 4/2003 | Kroll | 607/27 |
| 6,687,545 B1 * | 2/2004 | Lu | 607/28 |
| 6,714,819 B1 * | 3/2004 | Sloman | 607/28 |

(Continued)

FOREIGN PATENT DOCUMENTS

EP    1 136 098    * 9/2001

(Continued)

*Primary Examiner*—Carl H Layno
*Assistant Examiner*—Brian T. Gedeon
(74) *Attorney, Agent, or Firm*—Stephen W. Bauer

(57) ABSTRACT

A cardiac stimulation system and associated capture management method are provided in which a safety factor, used in setting pacing pulse output energy, is automatically adjusted in response to the detection of indicators of a likely increase in pacing threshold. The method includes monitoring for increased pacing threshold indicators, which may also be associated with a compromised ability to perform a pacing threshold search. Such indicators may include, but are not limited to, the presence of arrhythmias, arrhythmia episode duration, pacing mode switches, refractory sensed events, and/or lead impedance changes. In response to the detection of a selected indicator of increased pacing threshold, the safety factor is automatically increased. After an increased pacing threshold indicator has not be detected for an interval of time, or if a pacing threshold search yields a result, the safety factor may be restored to a programmed value.

24 Claims, 5 Drawing Sheets

U.S. PATENT DOCUMENTS

| | | | |
|---|---|---|---|
| 7,158,831 B2 * | 1/2007 | Zhu | 607/28 |
| 7,308,310 B1 * | 12/2007 | Levine et al. | 607/28 |
| 7,317,943 B2 * | 1/2008 | Ferek-Petric | 607/28 |
| 2004/0260352 A1 | 12/2004 | Rueter et al. | 607/28 |

FOREIGN PATENT DOCUMENTS

| | | |
|---|---|---|
| EP | 1 136 098 A2 | 9/2001 |
| WO | WO 2004/030748 A2 | 4/2004 |

* cited by examiner

DYNAMIC ADJUSTMENT OF CAPTURE MANAGEMENT "SAFETY MARGIN"

FIELD OF THE INVENTION

The present invention relates generally to the field of implantable cardiac stimulation devices and more particularly to an improved method for maintaining capture using an automatically adjusted safety factor for setting the pacing pulse energy.

BACKGROUND OF THE INVENTION

Cardiac stimulation devices deliver appropriately timed electrical stimulation pulses to a patient's heart to maintain a normal heart rhythm or improve synchronization of heart chambers. Patients having bradycardia, abnormalities of the heart's natural conduction system, a propensity for arrhythmias, cardiac-related breathing disorders, hemodynamic insufficiency, or other cardiac-related conditions may benefit from cardiac pacing therapies delivered in one or more heart chambers.

In order to effectively pace the heart, an electrical impulse delivered to the heart must have sufficient energy to depolarize the myocardial cells. Depolarization of the myocardial cells in response to a pacing pulse is often referred to as "capture." The cardiac electrogram signal evidencing capture, which is a P-wave in the atria or an R-wave in the ventricles, is generally referred to as an "evoked response." The lowest pacing pulse energy that captures the heart may be referred to as the "pacing threshold" or "capture threshold". The amplitude and duration of a pacing pulse are preferably set to produce a pacing pulse energy somewhat greater than the pacing threshold in order to ensure effective cardiac pacing.

However, in order to prolong the battery life of the implanted cardiac stimulation device, it is desirable to program the pacing pulse energy to be a minimum value that is considered safely above the pacing threshold. Therefore, the pacing pulse amplitude is commonly set equal to the measured pacing threshold multiplied by a "safety factor." The resulting pacing pulse amplitude setting provides a safety margin that ensures capture despite small fluctuations that may occur in the pacing threshold.

Pacing threshold can change over time due to tissue encapsulation of the pacing electrodes, lead movement, changes in the patient's clinical condition, changes in medical therapy, or other causes. A rise in pacing threshold can result in loss of capture and ineffective pacing therapy. Modern pacemakers typically include automatic pacing threshold search algorithms that automatically adjust the pacing pulse energy to ensure pacing pulses remain above the pacing threshold, even if it varies over time. A pacing threshold search may deliver pacing pulses starting at an initially high pulse energy that is greater than the pacing threshold and then progressively decrease the pulse energy until capture is lost. The lowest pulse energy at which capture still occurs is determined as the pacing threshold.

Thus, capture management systems typically include monitoring for changes in the pacing threshold and monitoring for evidence of capture during pacing. Capture monitoring may be performed continuously or periodically and typically involves sensing an evoked P-wave or R-wave following pacing pulse delivery. If loss of capture is detected, a pacing threshold search is performed and a new pacing pulse energy is set based on the pacing threshold search result and the programmed safety factor.

Situations may arise, however, when the pacing threshold is likely to be increased yet a pacing threshold search either fails or yields unreliable results. For example, during and after an episode of atrial fibrillation (AF) or atrial flutter (AFL), the atrial pacing threshold is typically increased. A pacing threshold search may be unsuccessful due to unstable thresholds and/or sensing. In another example, if a lead has shifted or become dislodged, the pacing threshold is likely to be increased, but a pacing threshold search may be unsuccessful due to sensing characteristics that have also changed. The programmed safety factor used in setting the pacing pulse energy may not be sufficient to ensure capture during these situations.

The safety factor is typically a fixed value that is programmable by the clinician. A dynamically variable safety margin is proposed in U.S. Pat. No. 6,456,882, issued to Schloss. An automatic capture/threshold capability is generally disclosed wherein the safety margin is periodically increased or decreased according to the performance of the stimulation device, i.e., based upon the frequency of capture. In U.S. Pat. No. 6,456,879, issued to Weinberg, a method is generally disclosed for altering stimulation energy based on rheobase and/or chronaxie shift of a strength-duration curve. The strength-duration curve may be divided into two regions having differently sized safety margins.

There remains a need, however, for recognizing situations in which a rise in pacing threshold can be expected yet a pacing threshold search may not yield a result for appropriately adjusting the pacing pulse energy.

BRIEF SUMMARY OF THE INVENTION

The present invention provides a cardiac stimulation system and associated capture management method that includes an automatically adjustable safety factor responsive to the detection of indicators of a likely increase in pacing threshold. The method includes monitoring for conditions that are likely to be associated with an increased pacing threshold, which may also be associated with a compromised ability to perform a pacing threshold search. Such conditions may include, but are not limited to, the presence of arrhythmias, arrhythmia episode duration, pacing mode switches, refractory sensed events or events triggered by refractory sensed events such as a non-competitive atrial pacing period, and/or lead impedance changes. In response to the detection of any of these selected conditions as increased pacing threshold indicators, the safety factor is automatically increased to a predetermined setting. The safety factor may be applied to the pulse amplitude setting and/or the pulse width setting such that the overall pulse energy is increased.

The increased safety factor may be allowed to decay over time or restored to a programmed value when detected indicators triggering the increase in the safety factor have not been detected for a period of time. The safety factor may also be restored to its programmed value if a pacing threshold search is successful.

The system includes an implantable cardiac stimulation device and a set of associated electrodes coupled to the device for sensing cardiac electrical activity and for delivering stimulation pulses. The stimulation device includes sensing circuitry for sensing cardiac electrical activity from signals received from the electrodes; output circuitry for delivering cardiac stimulation pulses via the electrodes; and a control system for controlling the delivery of stimulation pulses such as the amplitude and duration of the pulses, the timing of pulse delivery, and the electrodes used to deliver the pulses. The control system may include dedicated integrated circuitry and/or a microprocessor and associated memory for storing control programs to be executed by the microprocessor. The control system initiates pacing threshold searches; monitors for increased pacing threshold indicators; and manages the automatic adjustment of the safety factor in response to detecting or not detecting such indicators.

Thus the system and associated capture management method provided by the present invention allow the pacing pulse energy to be automatically increased according to an increased safety factor even when an increased pacing threshold is not measurable via a pacing threshold search. The methods of the present invention thereby ensure capture during situations that are associated with a rise in pacing threshold.

DETAILED DESCRIPTION OF THE PREFERRED EMBODIMENTS

The present invention is in one embodiment a capture management method wherein the safety factor used in setting the output pulse energy is automatically adjusted in response to detecting conditions that are often associated with an increase in pacing threshold. The present invention is useful in both atrial and/or ventricular stimulation applications. Thus, the present invention may be realized in single, dual, or multichamber cardiac stimulation devices, capable of delivering a cardiac pacing therapy. The term "cardiac pacing therapy" is used herein to refer to any cardiac stimulation therapy that employs relatively low-energy stimulation pulses to depolarize the myocardial tissue to achieve a therapeutic effect. Cardiac pacing therapies may include but are not limited to, bradycardia pacing, cardiac resynchronization therapy, extra systolic stimulation therapies, overdrive pacing for treating or preventing arrhythmias or cardiac-related disordered breathing, and anti-tachycardia pacing therapies.

Figure 1:
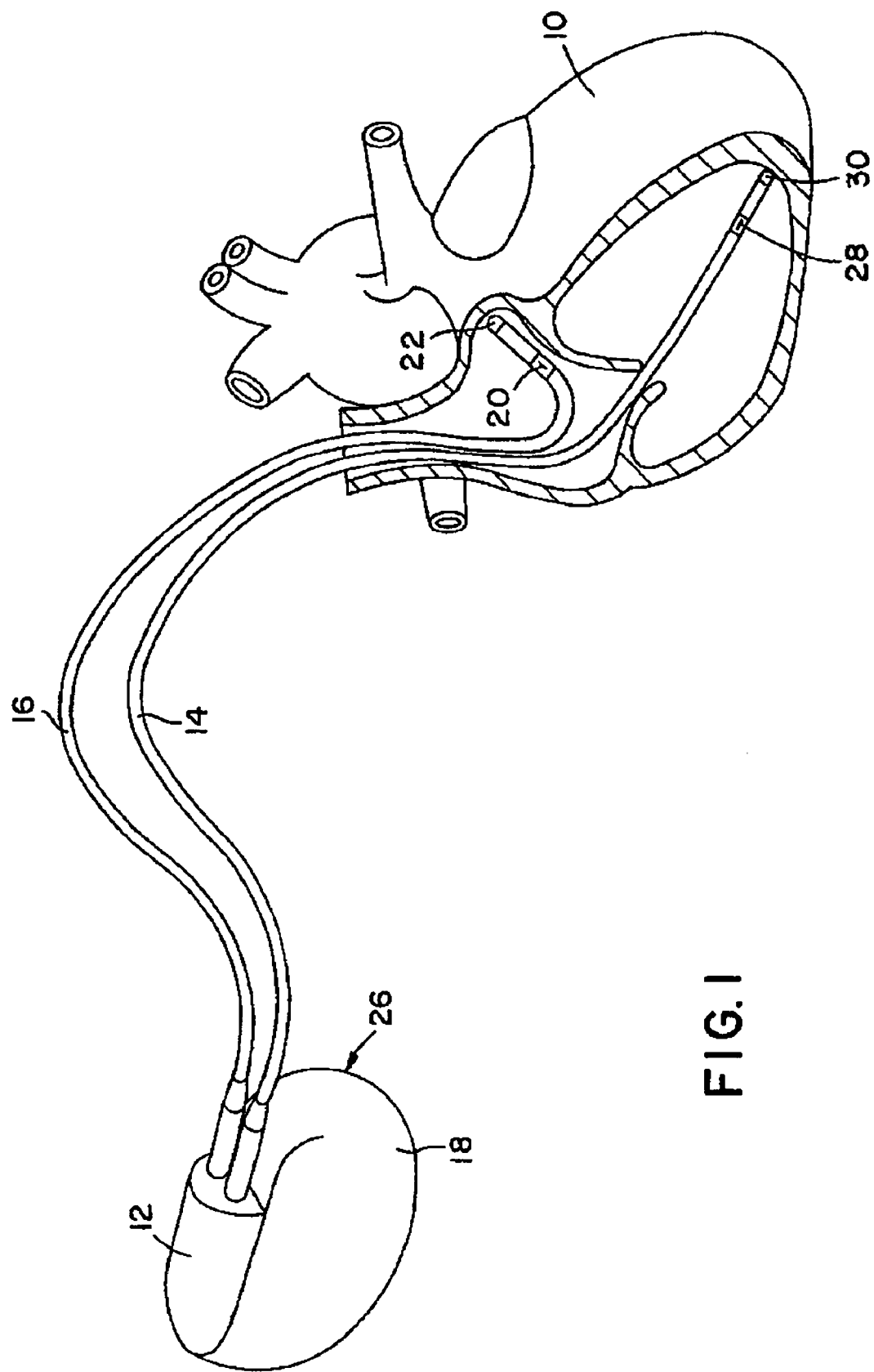
FIG. 1 is an illustration of an exemplary cardiac stimulation device in which the present invention may be usefully practiced.

FIG. 1 is an illustration of an exemplary cardiac stimulation device in which the present invention may be usefully practiced. FIG. 1 illustrates the external configuration of a dual chamber cardiac stimulation device 26, which is provided with a hermetically sealed enclosure 18, typically fabricated of biocompatible metal such as titanium. Mounted to the top of the enclosure 18 is a connector block assembly 12, which receives electrical connectors located on the proximal ends of leads 14 and 16. The combination of the leads 14 and 16 and the device 26 constitute an implantable cardiac stimulation system. A dual chamber cardiac stimulation device in which the present invention may be implemented is generally described in U.S. Pat. No. 5,507,782, issued to Kieval et al., which is hereby incorporated herein by reference.

Lead 16 is an atrial bipolar cardiac stimulation and sensing lead, carrying two electrodes 20 and 22. Electrodes 20 and 22 are used both to sense atrial depolarizations (P-waves) and to deliver atrial stimulation pulses. Atrial stimulation pulses may be delivered between electrodes 20 and 22 in a bipolar mode or between electrode 22 and the housing 18 of device 26 in a unipolar mode. Sensing of P-waves may occur between electrode 20 and electrode 22 in a bipolar sensing mode or between either of electrode 20 and 22 and the housing 18 of device 26 in a unipolar sensing mode.

Similarly, lead 14 represents a ventricular bipolar cardiac stimulation and sensing lead, carrying two electrodes 28 and 30. Electrodes 28 and 30 are used to sense and stimulate the ventricle. Sensing of ventricular depolarizations (R-waves) may be accomplished between electrodes 30 and 28 in a bipolar sensing mode or between either of electrodes 30 and 28 and the housing 18 of device 26 in a unipolar sensing mode. Bipolar ventricular stimulation may be accomplished between electrodes 30 and 28 or unipolar ventricular stimulation may be accomplished between electrode 30 and the conductive housing 18 of device 26.

Figure 2:
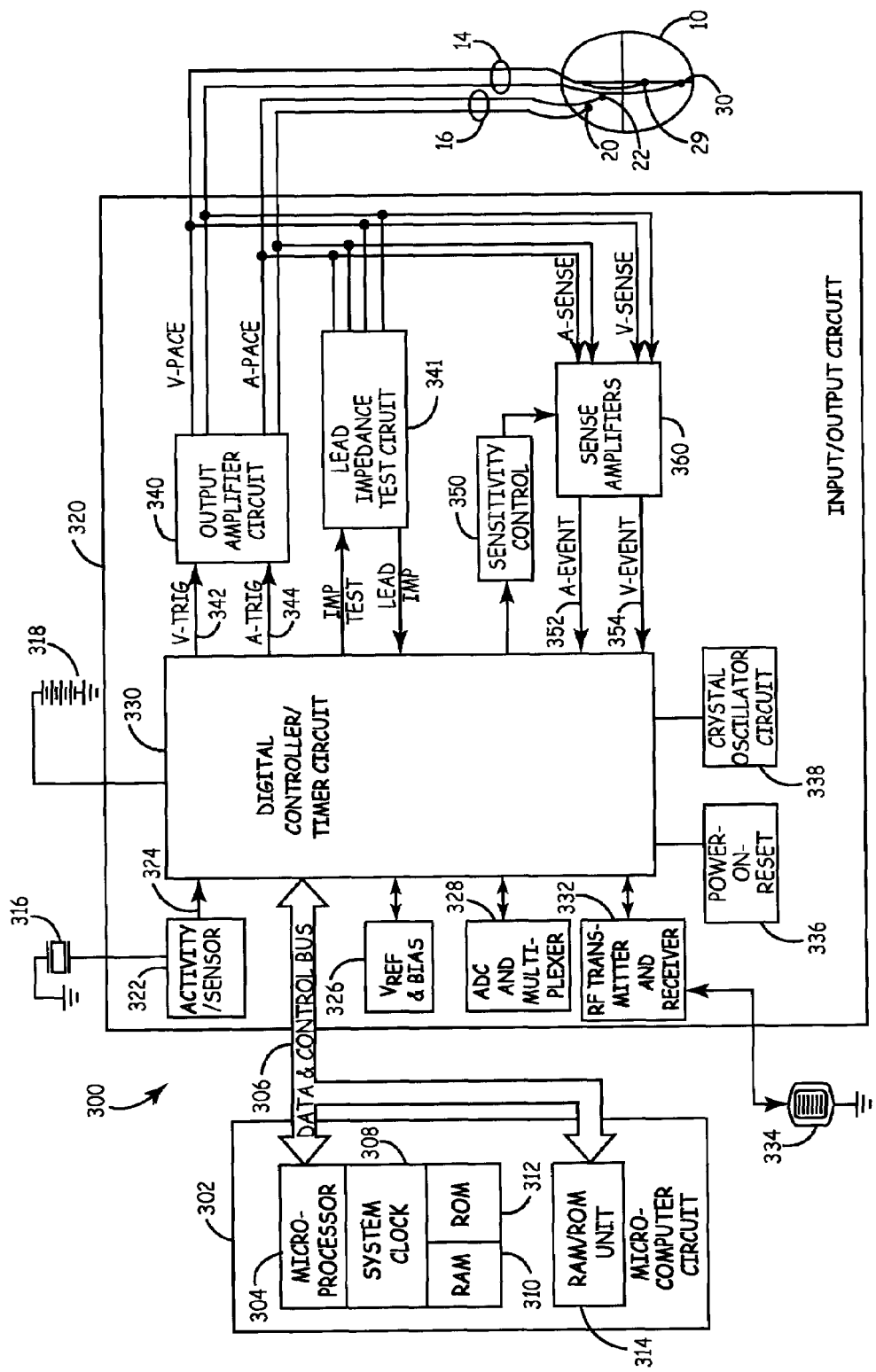
FIG. 2 is a more detailed functional block diagram of the cardiac stimulation device illustrated in FIG. 1.

FIG. 2 is a more detailed functional block diagram of the cardiac stimulation device illustrated in FIG. 1. The device circuit 300 is located within housing 18 of device 26 as illustrated in FIG. 1. The bipolar leads 14 and 16 are illustrated schematically as coupled directly to the input/output circuit 320. However, in the actual implantable device they would, of course, be coupled by means of removable electrical connectors inserted in the connector block 12 illustrated in FIG. 1.

Circuit 300 is divided generally into a microcomputer circuit 302 and an input/output circuit 320. An output amplifier circuit 340 includes a ventricular pulse generator circuit coupled to the ventricle of the heart 10 by means of electrodes 28 and 30 on lead 16 as well as an atrial pulse generator circuit coupled to the atrium of heart 10 by means of atrial electrodes 20 and 22, located on lead 14. Similarly, sense amplifier circuit 360 includes atrial and ventricular sense amplifiers coupled to the atrium and ventricle, respectively, by means of leads 14 and 16. The output circuit 340 and sense amplifier circuit 360 may contain pulse generators and sense amplifiers, respectively, corresponding to any of those presently employed in commercially available cardiac pacemakers.

Sensed atrial depolarizations (or P-waves) that are detected by the atrial sense amplifier, in response to an atrial signal received from atrial lead 14 exceeding an atrial P-wave sensing threshold, are communicated to the digital controller/timer circuit 330 on A-event line 352. Similarly, ventricular depolarizations (or R-waves) that are detected by the ventricular sense amplifier, in response to a ventricular signal received from ventricular lead 16 exceeding a ventricular R-wave sensing threshold, are communicated to the digital controller/timer circuit 330 on V-event line 354. In devices configured for the detection of arrhythmias, consecutively sensed R-waves and P-waves may be used for measuring various intervals, such as R—R intervals, P—P intervals, R-P intervals and P-R intervals, for use in detecting arrhythmias as will be described in greater detail below.

In the absence of a sensed event prior to the expiration of a related escape interval, a pacing pulse will be generated by input/output circuit 320. In order to trigger generation of a ventricular pacing pulse, digital controller/timer circuit 330 generates a trigger signal on V-trig line 342. Similarly, in order to trigger an atrial pacing pulse, digital controller/timer circuit 330 generates a trigger pulse on A-trig line 344.

Control of timing and other functions within the input/output circuit 320 is provided by digital controller/timer circuit 330, which includes a set of timers and associated logic. Digital controller/timer circuit 330 defines the basic pacing or escape intervals controlling the timing of atrial and ventricular pacing pulse delivery. An A—A escape interval is initiated on atrial sense (A-event) or atrial pace (A-pace) events. An atrial pacing pulse (A-pace) is triggered at the expiration of the A—A escape interval. A V—V escape interval is initiated on ventricular sense (V-event) or pace (V-pace) events, and a ventricular pulse pacing (V-pace) is triggered upon the expiration thereof. Digital controller/timer circuit 330 also defines A-V intervals that commence following a sensed A-event or a delivered A-pace, and upon the expiration thereof a ventricular pacing pulse is triggered during atrial synchronized pacing modes. The specific values of the escape intervals defined by timer circuit 330 are controlled by the microcomputer circuit 302 by means of data and control bus 306 according to programmed parameter values and operating modes.

A variety of mode switching features have been disclosed or implemented in commercially available devices which respond to an excessively rapid atrial rhythm by causing the pacing system to switch from an atrial synchronized pacing mode, such as DDD/DDDR, to a non-synchronized mode such as VVI/VVIR or DDI/DDIR. Such mode switching features are disclosed in U.S. Pat. No. 5,144,949, by Olson, U.S. Pat. No. 5,318,594, by Limousin et al., U.S. Pat. No. 4,944,298, by Sholder, and U.S. Pat. No. 4,932,406 by Berkovits, all incorporated herein by reference in their entireties. In such pacing systems, the primary purpose of the mode switch is to prevent the pacing system from tracking a non-physiologic atrial rate. In accordance with the present invention, a pacing mode switch may be used as an indicator of an increased pacing threshold. During rapid atrial rhythms, the atrial substrate may be more difficult to capture. A pacing threshold search may be difficult to perform due to altered sensing characteristics or a fluctuating threshold or undesirable to perform during a potentially unstable rhythm. Therefore, a pacing mode switch may be selected as indicator of increased atrial pacing threshold, to which the device 26 responds by increasing the safety factor used in setting the atrial pacing pulse energy.

Digital controller/timer circuit 330 also controls sensitivity settings of the sense amplifiers 360 by means of sensitivity control 350 and defines time intervals for controlling operation of the atrial and ventricular sense amplifiers in sense amplifier circuit 360. A number of blanking and refractory intervals are typically defined, as is well known in the art, for controlling the sensing functions of sense amplifiers 360 and for controlling how digital timer/controller circuit 330 responds to sensed events.

For example, an atrial refractory sensed event occurring during a post ventricular atrial refractory period (PVARP) may trigger a non-competitive atrial pacing (NCAP) period during which no atrial pacing pulse may occur. The non-competitive atrial pacing period is intended to prevent triggering of atrial tachycardia by an atrial pacing pulse delivered during the relative refractory period. In accordance with the present invention, the pacing pulse energy may be increased on the next pacing pulse delivered after a NCAP period. The pacing pulse energy may be increased by applying an increased safety factor to the pacing pulse amplitude setting and/or the pacing pulse width setting.

In the embodiment illustrated in FIG. 2, device 26 is provided with a sensor 316, which may be a piezoelectric sensor intended to monitor patient activity, in order to allow provision of rate responsive pacing, such that the defined pacing rate (A—A escape interval or V—V escape interval) increases with increased levels of sensed activity. Sensor 316 generates electrical signals in response to sensed physical activity which are processed by activity/sensor circuit 322 and provided to digital controller/timer circuit 330. Similarly, the present invention may be practiced in conjunction with alternate types of physiological sensors such as oxygen sensors, pressure sensors, pH sensors and respiration sensors, all known for use in providing rate responsive pacing capabilities. The present invention may also be practiced in non-rate responsive pacemakers.

In alternative embodiments, a physiological sensor 316 and corresponding activity/sensor circuit 322 may alternatively be used for monitoring cardiac hemodynamic performance, myocardial contractile performance, a metabolic state or other physiological condition. Physiological sensors known for use in conjunction with implanted devices may include blood pressure sensors, oxygen saturation sensors, pH sensors, temperature sensors, blood flow sensors, acoustical sensors, accelerometers, impedance sensors and so forth. Signals from such sensors may be processed for determining a need for therapy delivery or therapy adjustment as a physiological condition or metabolic need changes. In accordance with the present invention, physiological signals that may indicate a change in the cardiac substrate may also be used as indicators of increased pacing threshold.

Data transmission to and from an external device, commonly known in the art as a "programmer," is accomplished by means of telemetry antenna 334 and an associated RF transmitter and receiver 332, which serves both to demodulate received downlink telemetry and to transmit uplink telemetry. For the purposes of the present invention, telemetry circuitry for communicating with an external device may correspond to any telemetry system known for use with implantable medical devices.

Threshold data from pacing threshold searches may be stored in the RAM 310 or the RAM/ROM unit 314 of microcomputer 302 for later telemetry out on command of an external programmer. This data may be encoded in digital form and transmitted via RF transmitter 332 and antenna 334 to an external programmer for display and/or analysis in the form of atrial and ventricular strength-duration curves as described in U.S. Pat. No. 5,601,615, issued to Markowitz et al., hereby incorporated herein by reference in its entirety. Data pertaining to detected increased pacing threshold indicators which trigger safety factor adjustments, in accordance with the present invention, may also be stored in RAM 310 for later telemetry out for diagnostic and therapy management purposes.

Crystal oscillator circuit 338 provides the basic timing clock for the input/output circuit 320, while battery 318 provides power. Power-on-reset circuit 336 responds to initial connection of the circuit to the battery for defining an initial operating condition and similarly, resets the operative state of the device in response to detection of a low battery condition. Reference mode circuit 326 generates stable voltage reference and currents for the analog circuits within the input/output circuit 320, while analog to digital converter (ADC) and multiplexer circuit 328 digitizes analog signals and voltage to provide real time telemetry of cardiac signals from sense amplifiers 360, for uplink transmission via RF transmitter and receiver circuit 332. Voltage reference and bias circuit 326, ADC and multiplexer 328, power-on-reset circuit 336 and crystal oscillator circuit 338 may correspond to any of those presently used in currently available implantable cardiac stimulation devices.

Microcomputer 302 controls the operational functions of digital controller/timer 330, specifying which timing intervals are employed, and controlling the duration of the various timing intervals, via data and control bus 306. Microcomputer 302 contains a microprocessor 304 and associated system clock 308 and on-processor RAM and ROM chips 310 and 312, respectively. In addition, microcomputer circuit 302 includes a separate RAM/ROM chip 314 to provide additional memory capacity. Microprocessor 304 is interrupt driven, operating in a reduced power consumption mode normally, and awakened in response to defined interrupt events, which may include the A-trig, V-trig, A-event and V-event signals.

Microprocessor 304 controls the scheduling of pacing threshold searches, either on a periodic or triggered basis, which are then executed by input/output circuit 320. For example, a pacing threshold search may be executed upon detection of loss of capture. For the purposes of the present invention, prior art circuitry and methods for performing pacing threshold searches and capture detection may be implemented in conjunction with the present invention. Examples of appropriate pacing threshold searching methods are generally disclosed in the previously incorporated U.S. Pat. No. 5,601,615 to Markowitz, in U.S. Pat. No. 6,067,472 issued to Vonk et al., in U.S. Pat. No. 5,713,933 issued to Condie et al., or U.S. Pat. No. 6,430,441 issued to Levine et al., all of which patents are incorporated herein by reference in their entirety.

In accordance with the present invention, microprocessor 304 executes code stored in associated memory 310 and 312 for detecting indicators of increased pacing threshold and for automatically increasing the safety factor in response to an increased pacing threshold indicator detection. A newly adjusted safety factor is then used by digital timer and controller 330 to cause output circuit 340 to deliver pacing pulses at an output energy set according to the most recent pacing threshold search result and the newly adjusted safety factor.

Device 26 may further include lead impedance measuring circuitry 341 coupled to leads 14 and 16 for monitoring changes in lead impedance. Implantable medical devices capable of measuring and monitoring changes in lead impedance are generally disclosed in U.S. Pat. No. 5,201,865 issued to Kuehn, U.S. Pat. No. 5,741,311 issued to McVenes et al., and U.S. Pat. No. 6,317,633 issued to Jorgenson et al., all of which are incorporated herein by reference in their entirety. A change in lead impedance may occur as the result of shifting or dislodgement of a lead. Such a change may result in a change in pacing threshold and/or may alter sensing characteristics making pacing threshold searches and capture detection algorithms unreliable. As will be described below, a change in lead impedance may therefore be selected as an indicator of a likely increase in pacing threshold which may be used to trigger an adjustment of the safety factor used in setting the pacing pulse output energy.

The illustrated device block diagram of FIG. 2 is merely exemplary, and corresponds to the general functional organization of a typical multi-programmable microprocessor controlled DDD(R) cardiac pacemaker. It is believed that the present invention is readily practiced in the context of such a device, and that the present invention can therefore readily be practiced using the basic hardware of existing microprocessor controlled dual chamber pacemakers, as presently available, with the invention implemented primarily by means of modifications to the software stored in the ROM 312 of the microcomputer circuit 302. However, the present invention may also be usefully practiced by means of a full custom integrated circuit, for example, a circuit taking the form of a state machine as set forth in the above-cited Betzold et al. patent, in which a state counter serves to control an arithmetic logic unit to perform calculations according to a prescribed sequence of counter controlled steps. As such, the present invention should not be understood to be limited to a cardiac stimulation device having an architecture as illustrated in FIG. 2, and a circuit architecture as illustrated in FIG. 2 is not believed to be a prerequisite to enjoying the benefits of the present invention.

Furthermore, while a particular dual-chamber implantable cardiac stimulation device and lead system is shown in FIGS. 1 and 2, the present invention may be usefully practiced in other types of cardiac stimulation devices such as any single, dual or multi-chamber cardiac stimulation device capable of providing cardiac pacing therapies and may further include higher-voltage stimulation therapies for cardioversion and defibrillation. As such, other types of lead systems may be substituted for the particular lead system shown in FIG. 1 according to the type of cardiac stimulation device implanted. Unipolar, bipolar, and/or multipolar leads provided with tip, ring, and/or coil electrodes may be used. A lead system may be used to position electrodes within the heart or external to the heart such as epicardial or subcutaneous placements.

In some embodiments of the present invention, an indicator of increased pacing threshold may be related to the occurrence of an arrhythmia. For example, the atrial substrate is believed to be more difficult to capture after an episode of atrial fibrillation or atrial flutter. The time that the increased pacing threshold is expected to remain higher is thought to be related to the duration of the atrial arrhythmia episode. As such, device 26 may include arrhythmia detection capabilities.

The following exemplary arrhythmia detection method employs rate/interval based timing criteria as a basic mechanism for detecting the presence of a tachyarrhythmia. To this end, the device defines a set of rate ranges and associated software-defined counters to track the numbers of intervals falling within the defined ranges.

A first rate range may define a minimum R—R or P—P interval used for ventricular fibrillation (VF) or atrial fibrillation detection (AF), respectively, referred to as a "fibrillation detection interval" or "FDI". An associated VF or AF count preferably indicates how many of a first predetermined number of the preceding intervals were shorter than the FDI. A second rate range may include R—R or P—P intervals shorter than a lower tachycardia detection interval "TDI", and an associated VT count or AT count is incremented in response to an interval shorter than the TDI but longer than the FDI, is not affected by intervals shorter than the FDI, and is reset in response to intervals longer than the TDI. Optionally, the device may include a third rate range including intervals longer than the FDI interval, but shorter than a fast tachycardia interval (FTDI) which is intermediate the lower tachycardia detection interval (TDI) and the lower fibrillation detection interval (FDI).

For purposes of the present example, the interval counts may be used to signal detection of an associated arrhythmia (fibrillation, fast tachycardia or slow tachycardia) when they individually or in combination reach a predetermined value, referred to herein as "number of intervals to detect" or "NID". Each rate zone may have its own defined count and NID, for example "AFNID" for atrial fibrillation detection and "ATNID" for atrial tachycardia detection, or combined counts may be employed. These counts, along with other stored information reflective of the previous series of R—R, P—P, P-R, and R-P intervals such as information regarding the rapidity of onset, the stability of the detected intervals, the duration of continued detection of short intervals, the average interval duration and information derived from analysis of stored EGM segments are used to determine whether tachyarrhythmias are present and to distinguish between different types of tachyarrhythmias.

Other tachyarrhythmia detection methodologies, including detection methods as described in U.S. Pat. No. 5,991,656, issued to Olson, et al., U.S. Pat. No. 5,755,736, issued to Gillberg, et al., both incorporated herein by reference in their entireties, or other known ventricular and/or atrial tachyarrhythmia detection methods may be substituted. It is believed that the automatic safety factor adjustment feature provided by the present invention may be usefully practiced in conjunction with virtually any underlying rate-based arrhythmia detection scheme when arrhythmia detection is selected as an indicator of increased pacing threshold. Other exemplary detection schemes are described in U.S. Pat. No. 4,726,380, issued to Vollmann, U.S. Pat. No. 4,880,005, issued to Pless et al. and U.S. Pat. No. 4,830,006, issued to Haluska et al., incorporated by reference in their entireties herein.

In selecting indicators of increased pacing threshold, particular types of arrhythmias or arrhythmias that are sustained for a particular duration of time may be selected. When the particular type of arrhythmia or required arrhythmia episode duration is detected, an adjustment of the safety factor used in setting the pulse energy output is triggered, as will be described in greater detail below.

When device 26 shown in FIG. 2 is provided with arrhythmia detection capabilities, device 26 may further be equipped with anti-arrhythmia therapy capabilities. Anti-arrhythmia pacing therapies may be delivered by output amplifier circuit 340 under the control of digital controller/timer circuit 330. In accordance with one implementation of the present invention, detection of atrial fibrillation or atrial tachycardia will trigger an increase in the safety factor. Thus, any pacing delivered during and/or for at least a period following an atrial arrhythmia episode will be delivered using a pulse energy set according to the increased safety factor.

As noted previously, the automatically adjusted safety factor feature provided by the present invention may be implemented in a device that further includes high-voltage arrhythmia therapies for cardioversion or defibrillation. An exemplary cardiac pacing/cardioversion/defibrillation/device in which the present invention may be implemented is disclosed U.S. Pat. No. 5,545,186 issued to Olson et al., incorporated herein by reference in its entirety.

Figure 3:
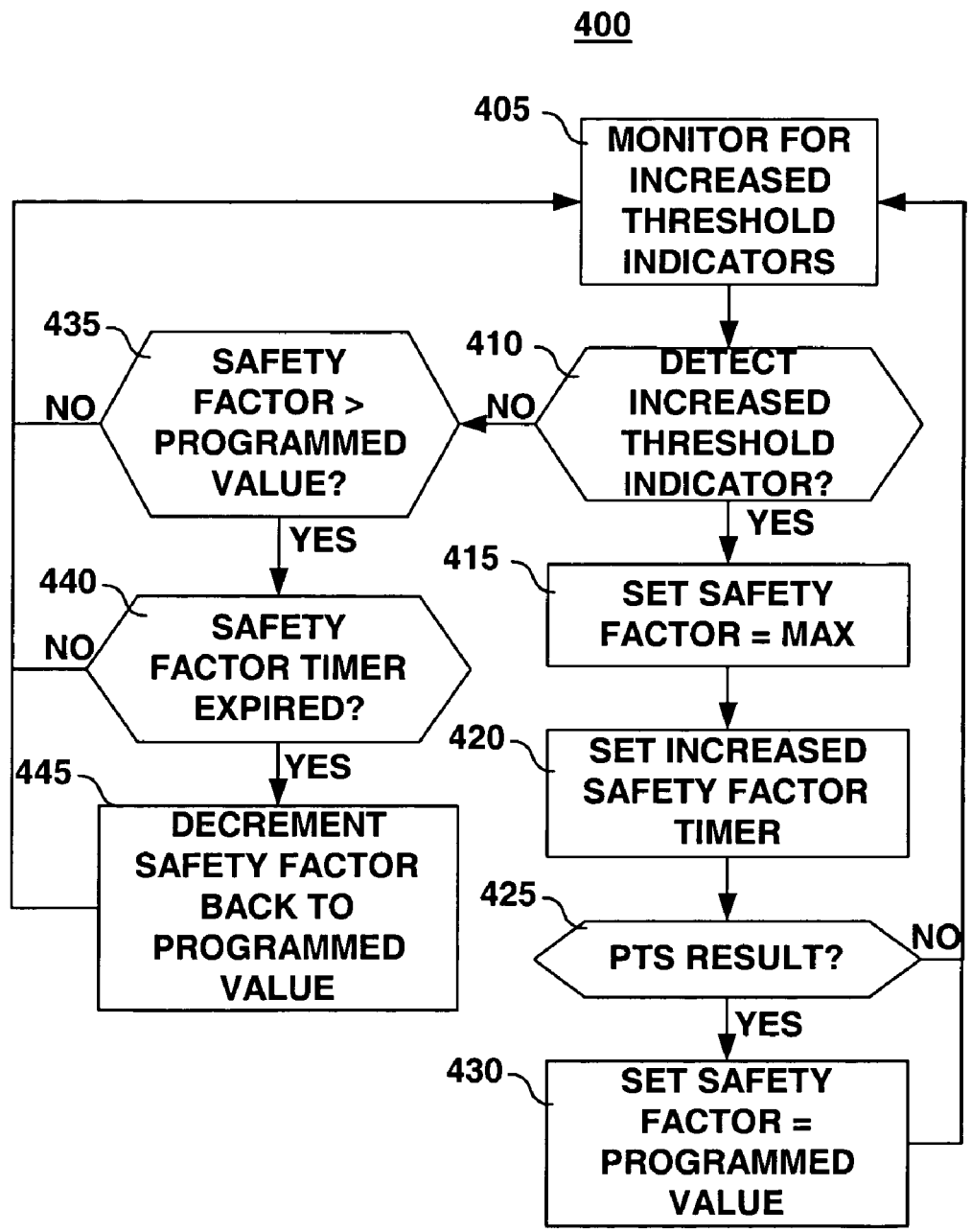
FIG. 3 is a flow chart providing an overview of a method for automatically adjusting the safety factor in response to detecting one or more indicators of a likely increase in pacing threshold in accordance with the present invention.

FIG. 3 is a flow chart providing an overview of a method for automatically adjusting the safety factor in response to detecting one or more indicators of a likely increase in pacing threshold in accordance with the present invention. Method 400 may be enabled by a clinician to operate continuously such that the safety factor is adjusted when in increased pacing threshold indicator is detected in order to ensure successful capture when and if a pacing therapy is delivered. Thus, method 400 may be operating even when a pacing therapy is not being delivered such that if a pacing therapy becomes necessary the pacing pulse energy delivered will be adequate to capture the heart tissue from the onset of pacing.

At step 405, microcomputer 302 monitors for events that have been previously defined as indicators of a likely increase in pacing threshold. Increased pacing threshold indicators may be selectable by a clinician and may include, but are not limited to, detection of an arrhythmia, the duration of an arrhythmia episode exceeding a predefined interval, a pacing mode switch, the duration of a pacing mode switch, a refractory sensed event or an event triggered by a refractory sensed event such as a non-competitive atrial pacing period, a lead impedance measurement that is outside a predefined normal lead impedance range, or a change in lead impedance greater than a predefined amount.

If any of the predefined increased threshold indicators are detected by microcomputer 302, as determined at decision step 410, the safety factor is increased to a predetermined maximum value at step 415. An increased safety factor may be applied for increasing the pacing pulse amplitude and/or the pacing pulse width. The maximum safety factor value may be a fixed maximum value, a multiple of the programmed safety factor, the programmed safety factor plus a predetermined increment, or some other function of the programmed safety factor. For example, the programmed safety factor may be set to 1.25 such that the pacing pulse amplitude and/or pulse width is set to 1.25 times the pacing threshold amplitude and/or pulse width. When an increased threshold indicator is detected, the safety factor may be doubled to 2.5 or adjusted to some other setting greater than the programmed value.

It is recognized that in some pacing applications, the pacing pulse energy may be set as the sum of a measured pacing threshold plus a "safety margin" rather than the product of a pacing threshold and a safety factor. It is to be understood that method 400 for increasing a safety factor in response to detecting an increased threshold indicator may equally be used for increasing a "safety margin" or any other parameter used to adjust the pacing output energy to a level that is safely above than a measured threshold in order to ensure capture.

At step 420 an increased safety factor timer may be set. The safety factor may be adjusted to an increased value for a predetermined period of time. The time interval for which the safety factor is increased may depend on the type of increased threshold indicator detected at step 405. For example, if an arrhythmia was detected that lasted several minutes or less, the increased safety factor timer may be set for an interval of only a few minutes. After the increased safety factor timer expires, the safety factor will be reset to its programmed value as will be described below. If an arrhythmia was detected that lasted several hours or even days, e.g., persistent AF or AFL, the increased safety factor timer may be set for an interval of several hours. In response to other events, such as a large increase in lead impedance, the increased safety factor may be set indefinitely or until clinician intervention. In response to a non-competitive atrial pacing period, the safety factor may be increased to effectively raise the pacing pulse energy for only a single pacing pulse following the NCAP period.

If, at any time after the safety factor has been increased, a pacing threshold search yields a result, as determined at decision step 425, the safety factor may be restored to its programmed value at step 430, and the pacing pulse energy adjusted accordingly. The increased safety factor is intended to ensure an adequate pacing pulse energy when an increased pacing threshold is suspected and a pacing threshold search cannot be performed successfully. Hence, if a valid pacing threshold result is available, the pulse energy may be adjusted appropriately using the programmed safety factor. After restoring the safety factor to the programmed value, method 400 returns to step 405 to monitor again for an increased threshold indicator.

If a pacing threshold search result is not available (decision step 425) at any time during the increased safety factor time interval, method 400 returns to step 405 to continue to monitor for increased threshold indicators. As long as an increased threshold indicator is detected to be present, the safety factor remains at the increased setting.

If an increased threshold indicator is not detected at decision step 410, method 400 proceeds to step 435. If the safety factor is not currently at an increased value, as determined at decision step 435, method 400 returns to step 405 to continue monitoring for increased threshold indicators. If the safety factor is currently greater than the programmed value, i.e., a previous increased threshold indicator detection has triggered an increase in the safety factor, method 400 determines if the safety factor timer has expired at step 440. If the safety factor timer has not expired, method 400 returns to step 405 to continue monitoring for increased threshold indicators.

Once no increased threshold indicators are detected (decision step 410) and the safety factor timer is expired (decision step 440), the safety factor may be adjusted back to the programmed valued at step 445. Thus, once conditions that are likely to cause a pacing threshold to be increased are no longer present, and an increased safety factor interval has expired during which time an elevated pacing threshold is expected to have returned to normal, the safety factor may be restored to the programmed value. The safety factor may be restored to the programmed value at step 445 in a single step adjustment or gradually in stepwise or exponential decrements.

Method 400 then returns to step 405 to continue monitoring for increased threshold indicators such that if an indicator is detected during or after the safety factor is adjusted back to a programmed value, the safety factor may again be increased to a maximum value.

Figure 4A:
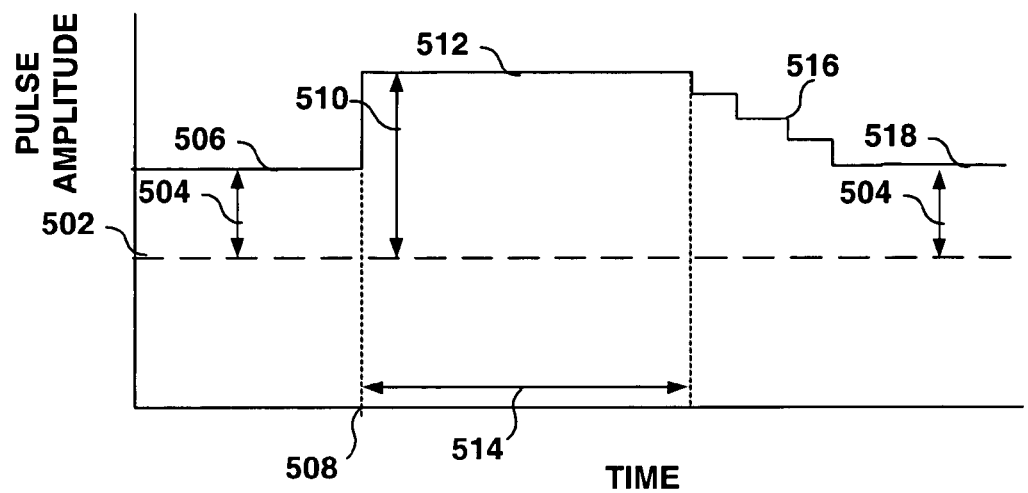
FIGS. 4A through 4C are plots of pulse amplitude changes over time which illustrate changes in the pulse amplitude that may be made in response to automatic adjustments to the safety factor in accordance with the method shown in FIG. 3.
Figure 4B:
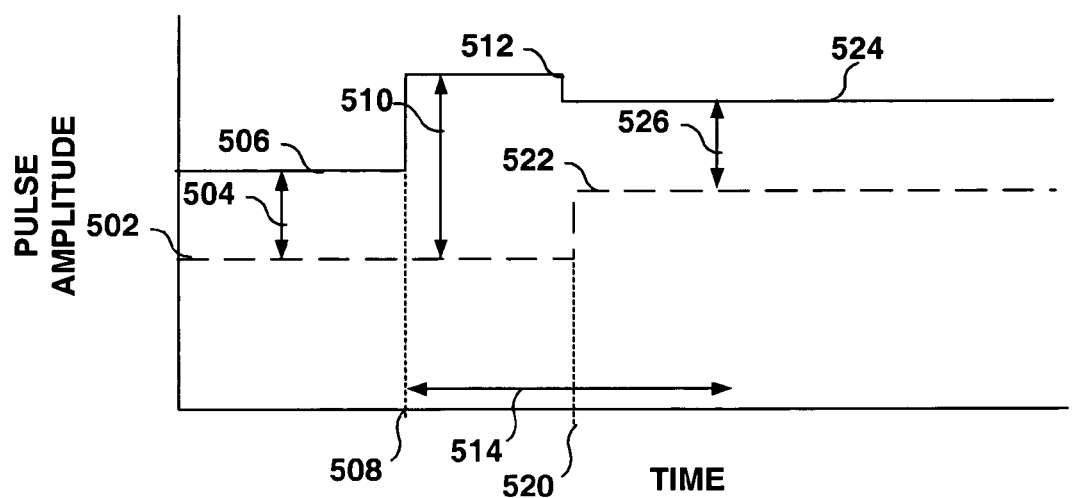
Figure 4C:
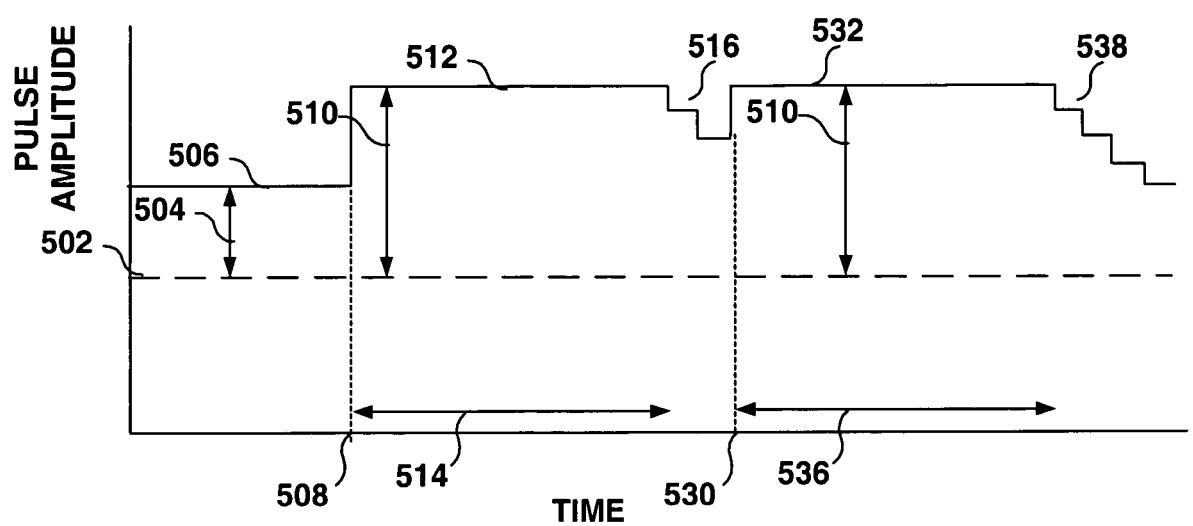

FIGS. 4A through 4C are plots of pulse amplitude changes over time which illustrate changes in the pulse amplitude that may be made in response to automatic adjustments to the safety factor in accordance with to the method shown in FIG. 3. In FIGS. 4A through 4C, pacing pulse amplitude is plotted over time. In these examples, the pacing pulse amplitude is shown to be adjusted in response to an automatically adjusted safety factor. However, it is recognized that either or both the pacing pulse amplitude and pacing pulse width may be increased to increase the overall pulse energy according to an increased safety factor or safety margin.

In FIG. 4A, a prior pacing threshold search yielded a pacing threshold 502 indicated by a horizontal dashed line. The pacing pulse amplitude is initially set at an amplitude 506 equal to the pacing threshold 502 multiplied by a programmed safety factor value. Pacing pulse amplitude 506 is thus set at a margin 504, safely above the threshold 502.

An increased threshold indicator is detected at time 508 triggering an increase in the safety factor. The pulse amplitude is reset to an increased amplitude 512 equal to the threshold 502 multiplied by the increased safety factor, providing a larger margin 510 above the threshold 502. At the end of an increased safety factor time interval 514, the safety factor is adjusted back to the programmed value. Such adjustment may be made in a stepwise or exponentially decreasing manner as described previously. Thus, the pulse amplitude is decreased at 516 as the safety factor is decreased (shown here in stepwise decrements), back to an amplitude 518 equal to the threshold 502 multiplied by the programmed safety factor value.

In FIG. 4B, an initial pacing pulse amplitude 506, set based on a previously measured pacing threshold 502 and a programmed safety factor value, is increased to amplitude 512 after detecting an increased threshold indicator at time 508. However, in the example shown in FIG. 4B, a pacing threshold search is performed at 520 yielding a new pacing threshold 522. The increased safety factor time interval 514 has not yet expired, however, the safety factor is restored to its programmed value upon measuring a pacing threshold successfully. The pacing pulse amplitude is adjusted to a new value 524 equal to the new threshold 522 multiplied by the programmed safety factor value, resulting in a margin 526 above the new threshold 522 corresponding to the programmed safety factor.

In the example shown in FIG. 4C, detection of an increased threshold indicator at 508 triggers an increase in the safety factor resulting in an increase in pulse amplitude from amplitude 506 to amplitude 512 as described previously. The safety factor is decreased after the increased safety factor time interval 514 expires, resulting in a decreasing pulse amplitude 516. However, prior to restoration of the programmed safety factor value, a second increased threshold indicator is detected at 530, causing the safety factor to be reset to a high setting and a correspondingly increased pulse amplitude 532. After expiration of a second increased safety factor time interval 536, without any intervening pacing threshold search results or new increased threshold indicator detections, the safety factor is adjusted back to the programmed value, and the pacing pulse amplitude is correspondingly decreased at 538.

Thus, a method for automatically adjusting the safety factor used in setting cardiac pacing pulse energy is provided for use in maintaining capture under conditions normally associated with an increased pacing threshold when an updated pacing threshold measurement may not be available. The detailed descriptions of the methods described herein are intended to illustrate the concept of the present invention. It is recognized that those skilled in the art, having the benefit of the teachings provided herein, may conceive of numerous variations to the methods described herein for automatically adjusting a safety factor or a safety margin in response to various indicators of an increased pacing threshold. The embodiments described herein are intended to be exemplary, therefore, and not limiting with regard to the following claims.

The invention claimed is:

1. A method of providing capture management in an implantable medical device, the method comprising:
   monitoring for indicators of a likely increase in pacing threshold in the absence of a pacing threshold search of the type that comprises delivering pacing pulses; and
   increasing a safety factor used in setting a pacing pulse output energy responsive to a said indicator of increased pacing threshold detected in the absence of a said pacing threshold search.

2. The method of claim 1 further comprising:
   setting a time interval during which the increased safety factor is maintained; and
   restoring the safety factor to a programmed value after the time interval has expired.

3. The method of claim 2, wherein the duration of the time interval is set according to the type of indicator of increased pacing threshold that has been detected.

4. The method of claim 2 further comprising:
   monitoring for indicators of increased threshold during the time interval; and
   resetting the time interval for which the increased safety factor is maintained if a second indicator of increased pacing threshold is detected.

5. The method of claim 1 further comprising:
   performing the pacing threshold search after detecting an indicator of increased pacing threshold; and
   reducing the increased safety factor back to a programmed value if the pacing threshold search yields a result.

6. The method of claim 1, wherein indicators of increased threshold include a change in lead impedance.

7. The method of claim 1, wherein increasing the safety factor comprises increasing the safety factor to a predetermined setting.

8. The method of claim 1, wherein increasing the safety factor comprises increasing the safety factor to a predetermined maximum safety factor value.

9. A method of providing capture management in an implantable medical device, the method comprising:
monitoring for arrhythmia detections in the absence of a pacing threshold search of the type that comprises delivering pacing pulses; and
increasing a safety factor used in setting a pacing pulse output energy responsive to said arrhythmia detections in the absence of a said pacing threshold search.

10. The method of claim 9, wherein the arrhythmia detections include arrhythmia detections exceeding a predetermined duration.

11. A method of providing capture management in an implantable medical device, the method comprising:
monitoring for pacing mode switches in the absence of a pacing threshold search of the type that comprises delivering pacing pulses; and
increasing a safety factor used in setting a pacing pulse output energy responsive to said pacing mode switches in the absence of a said pacing threshold search.

12. A method of providing capture management in an implantable medical device, the method comprising:
monitoring for indicators of a likely increase in pacing threshold in the absence of a pacing threshold search of the type that comprises delivering pacing pulses;
increasing a safety factor used in setting a pacing pulse output energy responsive to a said indicator of increased pacing threshold detected in the absence of a said pacing threshold search;
wherein said indicators of increased threshold include a refractory sensed events or events triggered by refractory sensed events in the absence of a pacing threshold search of the type that comprises delivering pacing pulses; and
increasing a safety factor used in setting a pacing pulse output energy responsive to said refractory sensed events or events triggered by refractory sensed events in the absence of a said pacing threshold search.

13. An implantable medical device comprising:
a pulse generator for delivering pacing pulses;
at least one electrode in electrical communication with the pulse generator for delivering the pacing pulses to cardiac tissue; and
a microprocessor for controlling the pulse generator, receiving sensed data from the at least one electrode, wherein the sensed data includes an indicator of increased pacing threshold, wherein the sensed data is generated in the absence of a pacing threshold search of the type that comprises delivery of the pacing pulses, and increasing a safety factor used for setting the pacing pulse energy delivered by the pulse generator when the responsive to a said indicator of increased pacing threshold detected in the absence of a said pacing threshold search.

14. An implantable medical device (IMD) comprising:
means for monitoring for indicators of a likely increase in pacing threshold in the absence of a pacing threshold search of the type that comprises delivering pacing pulses; and
means for increasing a safety factor used in setting a pacing pulse output energy responsive to a said indicator of increased pacing threshold detected in the absence of a said pacing threshold search.

15. The IMD of claim 14 further comprising:
means for setting a time interval during which the increased safety factor is maintained; and
means for restoring the safety factor to a programmed value after the time interval has expired.

16. The IMD of claim 15, wherein the duration of the time interval is set according to the type of indicator of increased pacing threshold that has been detected.

17. The IMD of claim 15, wherein indicators of increased pacing threshold include a change in lead impedance.

18. The IMD of claim 14 further comprising:
means for performing the pacing threshold search after detecting an indicator of increased pacing threshold; and
means for reducing the increased safety factor back to a programmed value if the pacing threshold search yields a result.

19. An implantable medical device (IMD) comprising:
means for monitoring for arrhythmia detections in the absence of a pacing threshold search of the type that comprises delivering pacing pulses;
means for increasing a safety factor used in setting a pacing pulse output energy responsive to said arrhythmia detections in the absence of a said pacing threshold search;
means for setting a time interval during which the increased safety factor is maintained; and
means for restoring the safety factor to a programmed value after the time interval has expired.

20. The IMD of claim 19, wherein the arrhythmia detections include arrhythmia detections exceeding a predetermined duration.

21. An implantable medical device (IMD) comprising:
means for monitoring for pacing mode switches in the absence of a pacing threshold search of the type that comprises delivering pacing pulses;
means for increasing a safety factor used in setting a pacing pulse output energy responsive to said pacing mode switches in the absence of a said pacing threshold search;
means for setting a time interval during which the increased safety factor is maintained; and
means for restoring the safety factor to a programmed value after the time interval has expired.

22. An implantable medical device (IMD) comprising:
means for monitoring for refractory sensed events or events triggered by a refractory sensed events in the absence of a pacing threshold search of the type that comprises delivering pacing pulses;
means for increasing a safety factor used in setting a pacing pulse output energy responsive to said refractory sensed events or events triggered by a refractory sensed events in the absence of a said pacing threshold search;
means for setting a time interval during which the increased safety factor is maintained; and
means for restoring the safety factor to a programmed value after the time interval has expired.

23. The implantable medical device of claim 13, wherein the at least one electrode is coupled to a lead, and the indicator comprises at least one of an arrhythmia detection, an arrhythmia episode duration, a pacing mode switch of the pulse generator, a refractory sensed event or an impedance change of the lead.

24. An implantable medical device comprising:
a pulse generator that delivers pacing pulses;

at least one electrode in electrical communication with the pulse generator, wherein the at least one electrode is configured to deliver the pacing pulses to cardiac tissue; and a microprocessor that controls the pulse generator, receives sensed data from the at least one electrode, wherein the sensed data includes an indicator of increased pacing threshold, and wherein the indicator is associated with a compromised ability of the microprocessor to perform a pacing threshold search of the type that comprises delivery of the pacing pulses, and increase a safety factor used for setting the pacing pulse energy delivered by the pulse generator when the indicator of increased pacing threshold is detected.

* * * * *